United States Patent [19]

Linder et al.

[11] Patent Number: 4,496,455

[45] Date of Patent: Jan. 29, 1985

[54] POLAROGRAPHIC SENSOR AND SENSING SYSTEM FOR DETERMINING OXYGEN CONTENT IN GASES

[75] Inventors: Ernst Linder, Mühlacker; Helmut Maurer, Vaihingen; Klaus Müller, Tamm; Franz Rieger, Aalen, all of Fed. Rep. of Germany

[73] Assignee: Robert Bosch GmbH, Stuttgart, Fed. Rep. of Germany

[21] Appl. No.: 604,985

[22] Filed: Apr. 27, 1984

[30] Foreign Application Priority Data

Apr. 29, 1983 [DE] Fed. Rep. of Germany ....... 3315654

[51] Int. Cl.³ ............................................. G01N 27/58
[52] U.S. Cl. .................................... 204/412; 204/425
[58] Field of Search ................. 204/412, 425, 426, 1 S

[56] References Cited

U.S. PATENT DOCUMENTS 4,356,065 10/1982 Dietz .................................. 204/1 T
4,391,691 7/1983 Linder et al. ...................... 204/408

Primary Examiner—G. L. Kaplan
Attorney, Agent, or Firm—Frishauf, Holtz, Goodman & Woodward

[57] ABSTRACT

The linearity of response of a polarographic sensor, of the diffusion-limited current type, having a solid electrolyte (1) and being particularly adapted for measuring oxygen content in exhaust gases from combustion processes, is improved by providing the anode (2b) of the sensor's first, measuring cell with a constant, internal supply of reference oxygen. Preventing the oxygen concentration at the anode (2b) from fluctuating eliminates a non-linearity which would otherwise occur in the plot of oxygen concentration versus diffusion-limited current, as the fuel/air ratio of the mixture being combusted passes 1.

The oxygen supply takes the form of a second, pumping cell (3a, 3b) which can utilize the same solid electrolyte layer (1) as the first cell, and which pumps oxygen ions across the electrolyte to the second cell's anode (3b), where they become oxygen molecules and are directed through a duct (8) to the measuring cell's anode (2b).

Excessive pressure in the duct (8) is prevented by providing small pores (10) in the surrounding glass cover (9) for outward diffusion of excess oxygen. A constant voltage is applied to both cells.

7 Claims, 3 Drawing Figures

POLAROGRAPHIC SENSOR AND SENSING SYSTEM FOR DETERMINING OXYGEN CONTENT IN GASES

Cross-reference to related patent, assigned to the assignee of the present application, hereby incorporated by reference: U.S. Pat. No. 4,356,065, Oct. 26, 1982, DIETZ.

The present invention relates generally to polarographic sensors in which the output current of a measuring cell is limited by the amount of oxygen which diffuses through a porous layer to the cell cathode, and more particularly to sensors in which a solid electrolyte is sandwiched between measuring electrodes. Specifically, both a measuring cell and an oxygen pumping cell are sandwiched around the same solid electrolyte.

BACKGROUND

In polarographic sensors and sensing systems of this kind, the diffusion-limited current is measured at a constant voltage applied across the electrodes of the sensor's measuring cell. In an exhaust gas emitted by a combustion process using a lean mixture, this current is dependent upon the oxygen concentration, as long as the diffusion of the gas to the cathode determines the speed of the reaction which is taking place. It has already been proposed that polarographic sensors of this kind be designed in such a manner that both the anode and the cathode are exposed to the gas that is to be measured. The cathode then bears a diffusion barrier, in order to attain functioning in the diffusion-limited current range. The anode is exposed to the gas be measured, without having any such diffusion barrier, so that a constant oxygen partial pressure does not prevail at this anode, which serves as a reference electrode. This is disadvantageous for measurement in the lean range, because at a fuel/air mixture ratio (lambda)=1, the characteristic curve has a current jump, rather than extending over a steady course from lean mixture to rich mixture.

THE INVENTION

It is accordingly the object of the present invention to improve the polarographic sensor and sensing system as described above in such a manner that by creating an internal oxygen reference, the signal of the sensor extends on a steady course from lean to rich, no longer having a current jump in this curve. A particularly important fact is that this oxygen reference is attained without having to furnish a means of communication with the ambient air. This fact results in a simplification of the sensor structure and greater flexibility in the selection of where to install the sensor as compared with sensors in which the anode communicates with the ambient air, as an oxygen reference. A second, pumping cell supplies the oxygen.

Further advantages developments and improvements of the sensor are also possible within the scope of the invention. It is particularly advantageous to embody the duct connecting the two anodes as a porous layer covered by a gas-tight layer. This gas-tight layer has fine pores above the anode of the first cell, serving as a means of excess pressure limitation inside the porous layer.

DRAWINGS

FIG. 1 is a section taken through the tip of a sensor according to the invention in plate form;
FIG. 2 shows a plan view from below; and
FIG. 3 shows a plan view from above.

DESCRIPTION OF THE PREFERRED EMBODIMENT

Figure 1:
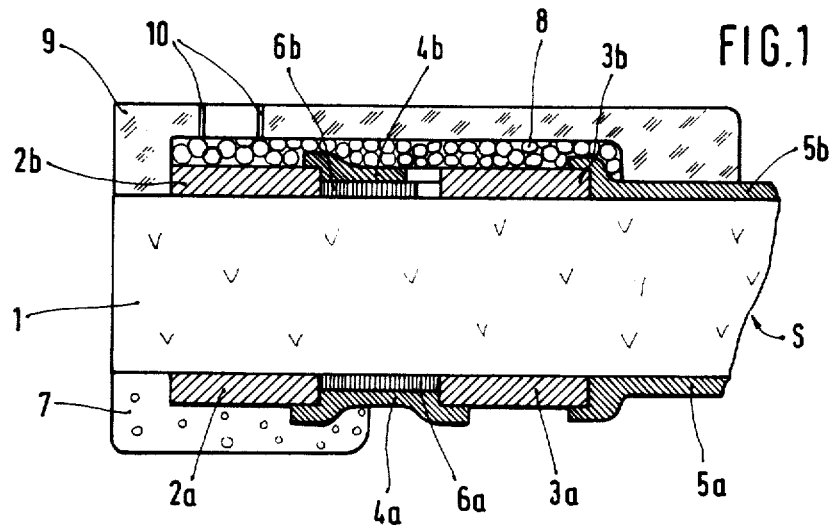

The sensor element S is made of a solid electrolyte plate 1, by way of example 50 mm $\times$ 8 mm $\times$ 1 mm in size, of stabilized zirconium dioxide. This plate carries two electrodes 2a and 2b, which are made of either platinum or a mixture of platinum and stabilized zirconium dioxide, the zirconium dioxide accounting for approximately 40% thereof by volume. This first cell, made of the electrodes 2a and 2b as well as the electrolyte 1, represents the actual measuring cell, to which a direct voltage of some volts is applied in such a manner that the electrode 2a acts as the cathode and the electrode 2b acts as the anode. The cathode 2a is entirely covered by a layer 7 having pores or ducts, a so-called diffusion barrier, of approximately 15 $\mu$m thickness, which is disposed in such a manner that the gas can pass through to the cathode 2a only through this diffusion barrier. The diffusion barrier 7 is for instance likewise made of zirconium dioxide and has a porosity such that the portion of the complete sensor, embodied by the cathode 2a and anode 2b as well as the solid electrolyte body 1, functions in the limiting current range over the widest possible oxygen partial pressure range. In order to form the second cell, the solid electrolyte plate 1 has, spaced apart somewhat from the electrodes 2a and 2b, two further electrodes 3a and 3b, which are designed in the same manner and the electrodes previously described. In this second cell, the electrode 3a acts as the cathode and the electrode 3b acts as the anode. Between the two cathodes 2a and 3a, an insulating layer 6a of aluminum oxide is first applied, and this layer 6a in turn carries a conductive path 4a, which is drawn partway over the electrode 2a and 3a and connects them electrically. A further conductive path 5a is applied to the reverse side of the electrode 3a and performs the function of electrically contacting of the two cathodes 2a and 3a. Between the two electrodes 2b and 3b, there is first another insulating layer 6b of aluminum oxide on the solid electrolyte, and this layer 6b carries a further conductive path 4b for contacting the electrode 2b; however, it does not touch the electrode 3b. The contacting of the electrode 3b is effected via a further conductive path 5b. The conductive paths may likewise be made of platinum or a mixture of platinum and zirconium dioxide or some other electrically conductive material. A highly porous layer 8, which for instance may be made of aluminum oxide with a high proportion of some pore-forming agent such as ammonium carbonate, is located over the electrodes 2b and 3b as well as the conductive path 4b. This porous layer 8 is coated with a gas-tight layer 9 made of a recrystallizing glass, such as alkaline earth silicate glass, with this layer 9 reaching around the electrode 2b and extending as far as the solid electrolyte 1, while on the other end another part of the conductive path 5b is also covered with this layer.

Figure 2:
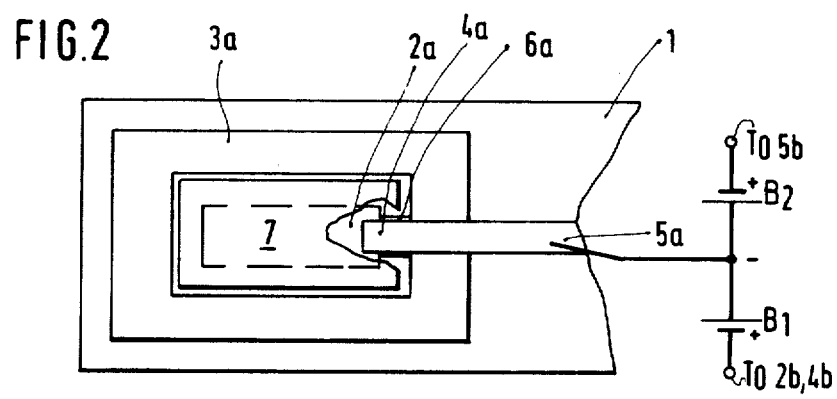
Figure 3:
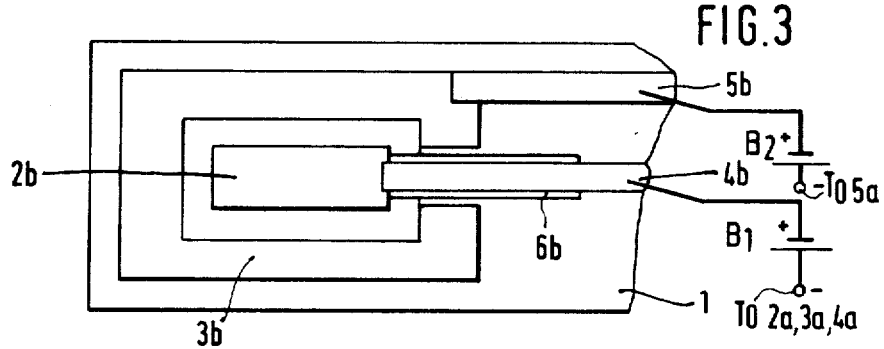

FIG. 2 shows a plan view on the cathode side of the plate-like sensor, while FIG. 3 shows the anode side. As seen in the drawing, the electrodes 2a and 2b are disposed centrally on the tip of the sensor. The electrode 3a is realized in the form of a ring and the electrode 3b is realized in the form of a U. Because of this disposition, the conductive paths 4a and 5a can be combined into one continuous strip. On the anode side, the conductive paths 4b and 5b take separate courses. The cathode 2a is covered by the diffusion barrier 7. In FIG. 3, which shows the anode side, the layers 8 and 9 were omitted from the drawing.

A direct voltage source B1 of approximately one volt is applied to the conductive paths 5a and 4b; this voltage furnishes the diffusion limiting current for measuring the oxygen concentration between the electrodes 2a and 2b. A further direct voltage source B2 of approximately one volt is applied to the conductive paths 5a and 5b, in such a way that for both cases the negative pole of the direct voltage sources rests on the conductive path 5a. The direct voltage source B2 between the conductive path connections 5a and 5b now causes a so-called pumping current, which assures that oxygen molecules travel in the form of ions from the electrode 3a through the solid electrolyte 1 to the electrode 3b, are discharged there and are thus available as oxygen molecules. These oxygen molecules, which are present in greater numbers here than at the electrode 2b, because in contrast to the electrode 2a the electrode 3a does not have any diffusion barrier and the oxygen molecules of the gas to be measured therefore have unhindered access to the electrode 3a, travel through the porous layer 8 as far as the electrode 2b, where the fine pores 10 prevent an excess oxygen pressure. An oxygen excess does, however, prevail at the electrode 2b, so that the cell made up of the electrodes 2a and 2b as well as the solid electrolyte 1 is capable of functioning with an oxygen excess, that is, an oxygen reference at the electrode 2b, without a means of communication with the oxygen of the ambient air having to be provided.

Circuits for evaluating the signals produced by the sensor, to determine the oxygen content of the test gases, have been omitted, because they are not necessary for an understanding of the present invention, and may be of conventional construction.

We claim:

1. Polarographic sensor system to determine oxygen content in test gases having
a sensor element (S) exposed to the test gases and a first current source (B1),
said sensor element comprising
a solid electrolyte body (1);
a first cell including
a cathode (2a);
a gas diffusion layer (7) exposed to the test gases and covering said cathode; and
an anode (2b);
the first current source (B1) being connected across the cathode and anode to cause a limit current to flow therethrough,
and comprising, in accordance with the invention,
a second cell including a cathode (3a) and an anode (3b);
means (8,9) to define an oxygen molecule communication duct between the anode (2b) of the first cell and the anode (3b) of the second cell,
the cathode (3a) of the second cell being exposed to the test gas; and
a second current source (B2) connected across the cathode (3a) and anode (3b) of the second cell to provide pumping energy for oxygen molecules to the anode of the second cell,
the communication duct (8,9) guiding pumped oxygen to the anode (2b) of the first cell.

2. The sensor of claim 1, wherein said duct-defining means comprises
a layer of porous material (8), and
a layer of gas-tight material (9) forming a cover over said porous material.

3. The sensor of claim 2, further comprising
means for limiting excessive pressure inside said gas-tight layer (9).

4. The sensor of claim 3, wherein said pressure limiting means comprises
fine pores (10) through said gas-tight material (9) between the anode (2b) of said first cell and ambient air.

5. The sensor of claim 1, further comprising
a conductive path (4a) connecting said cathodes (2a) and (3a),
a conductive path (5a) commonly connecting said cathodes to said current sources, and
separate conductive paths (4b) and (5b) connected respectively to the anode (2b) of said first cell and to the anode (3b) of said second cell.

6. The sensor of claim 5, wherein the conductive paths (4a) and (4b) connected to the electrodes (2a.2b) of said first cell are electrically insulated by respective nonconductive layers (6a) and (6b) from said solid electrolyte body (1).

7. Polarographic sensor system to determine oxygen content in test gases having
a sensor element (S) exposed to the test gases,
said sensor element comprising
a solid electrolyte body (1);
a first cell, adapted to be connected to a first current source B1, and including
a cathode (2a);
a gas diffusion layer (7) exposed to the test gases and covering said cathode; and
an anode (2b);
and comprising, in accordance with the invention,
a second cell, adapted to be connected to a second current source B2, and including a cathode (3a) and an anode (3b);
means (8,9) to define an oxygen molecule communication duct between the anode (2b) of the first cell and the anode (3b) of the second cell,
the cathode (3a) of the second cell being exposed to the test gas;
to provide, upon connection of the current sources, for current limit operation of the first cell and for pumping of oxygen molecules to the anode of the second cell,
the communication duct (8,9) guiding pumped oxygen to the anode (2b) of the first cell.

* * * * *